United States Patent [19]

Sweeney

[11] Patent Number: 5,059,734

[45] Date of Patent: Oct. 22, 1991

[54] PROCESS FOR SELECTIVELY PRODUCING C5 TO C18 STRAIGHT CHAIN α OLEFINS

[75] Inventor: William A. Sweeney, Larkspur, Calif.

[73] Assignee: Chevron Research and Technology Company, San Francisco, Calif.

[21] Appl. No.: 542,297

[22] Filed: Jun. 22, 1990

[51] Int. Cl.$^5$ .............................................. C07C 1/00
[52] U.S. Cl. ................................ 585/324; 585/510; 585/520; 585/639; 585/643; 585/644; 585/648; 585/653
[58] Field of Search ............... 585/639, 648, 500, 324, 585/328, 510, 520, 643, 644, 653

[56] References Cited

U.S. PATENT DOCUMENTS

| 3,283,027 | 11/1966 | Lundeen et al. | 260/682 |
|---|---|---|---|
| 3,600,455 | 8/1971 | Dean | 260/682 |
| 4,234,752 | 11/1980 | Wa et al. | 585/640 |
| 4,270,015 | 5/1981 | Knifton | 585/324 |
| 4,490,567 | 12/1984 | Drake | 585/324 |

FOREIGN PATENT DOCUMENTS

| 0222356 | 5/1987 | European Pat. Off. |
| 0150832 | 2/1988 | European Pat. Off. |
| 1233020 | 5/1971 | United Kingdom |

OTHER PUBLICATIONS

Lundeen et al., *Jorg Chem*, vol. 32, 1967, pp. 3386-3389.
Davis, *American Chemical Society*, vol. 18, No. 3, 1979, pp. 191-198.
Che et al., *Elsevier Science Publishers B.V.*, Amsterdam, 1985, pp. 309-318.

*Primary Examiner*—Curtis R. Davis
*Attorney, Agent, or Firm*—Richard J. Sheridan; Tom G. DeJonghe

[57] ABSTRACT

Disclosed is a process for preparing $C_5$ to $C_{18}$ straight chain α-olefins from the corresponding internal olefins. The process comprises reacting a $C_5$ to $C_{18}$ straight chain olefin reactant with an electrophilic compound containing hydrogen followed by selectively cracking the resulting product.

13 Claims, No Drawings

PROCESS FOR SELECTIVELY PRODUCING C5 TO C18 STRAIGHT CHAIN α OLEFINS

BACKGROUND OF THE INVENTION

1. Field of the Invention

The present invention relates to a method for selectively producing $C_5$ to $C_{18}$ straight chain α-olefins

2. Description of the Prior Art

Compounds having a terminal double bond (hereinafter referred to as "terminal olefins" or "α-olefins") are very useful industrially as raw materials for heat-resistant polymers, comonomers for the production of polyolefins, starting materials for detergents and so forth. The terminal olefin 1-hexene is especially valuable for many uses such as dimerization to dodecenes which are suitable for making biodegradable detergents, using it as a feed for the OXO reaction to make relatively linear $C_7$ alcohols, and as a comonomer in making linear low density polyethylene.

A potential source of 1-hexene is a mixture of n-hexenes which contains 1-hexene, cis and trans 2-hexene, and cis and trans 3-hexene. Unfortunately, however, the amount of 1-hexene in these mixtures is normally very low. For example, thermodynamic equilibration of n-hexenes produces a mixture containing only about 2-4% 1-hexene. While it is possible to separate the 1-hexene from the other n-hexenes in these mixtures, due to the very low levels of 1-hexene, such a procedure would be uneconomical. Thus, there exists a need for a method by which the amount of 1-hexene in these n-hexene mixtures can be substantially increased.

A known method for producing terminal olefins, such as 1-hexene, is to dehydrate a 2-alcohol, i.e., a compound of the formula

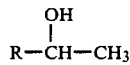

where R is a hydrocarbyl group. For example, U.S. Pat. No. 3,283,027, issued Nov. 1, 1966 to Lundeen et al., discloses the dehydration of 2-alcohols to terminal olefins using a catalyst which is a thorium, scandium, yttrium or rare earth oxide. While this dehydration reaction can produce an α-olefin and/or a 2-olefin, the Lundeen et al. product is said to be 90% or more α-olefin.

U.S. Pat. No. 3,600,455, issued Aug. 17, 1971, to Dean, discloses a process for producing the terminal olefin 4-methyl pentene-1 by dehydrating 4-methyl pentanol-1 or 4-methyl pentanol-2 by passing it over an alkalized alumina catalyst.

U.S. Pat. No. 4,234,752, issued Nov. 18, 1980, to Wu et al., discloses the dehydration of $C_{2-20}$ alcohols in the presence of gamma-alumina (which may be base-treated) employing an inert carrier gas to produce an olefin. The process is said to minimize isomerization which can convert desired products to undesired products. For example, according to Wu et al., 3-methyl-1-butanol can be dehydrated by this process to produce 3-methyl-1-butene having a 97.7 wt. % purity.

U.S. Pat. No. 4,490,567, issued Dec. 25, 1984, to Drake, discloses a process for the selective dehydration of 2-alcohols to α-olefins using a catalyst which is (1) at least one catalytic metal oxide on a low surface area aluminum oxide-containing support, or (2) a mixture of thorium oxide and cerium oxide on a base-treated aluminum oxide-containing support. Also described is a process for obtaining high purity 4-methyl-1-pentene by the dehydration of 4-methyl-2-pentanol followed by disproportionation with ethylene.

European Patent Specification Publication No. 0150832, published Nov. 2, 1988, discloses a process for preparing α-olefins by dehydrating 2-alcohols using a high purity (i.e., substantially free of silicon and titanium) zirconium oxide catalyst, and European Patent Specification Publication No. 0222356, published May 20, 1987, discloses the dehydration of 2-alcohols to α-olefins using a zirconia catalyst which has been treated with an alkaline solution.

Lundeen and Hoozer, "Selective Catalytic Dehydration. Thoria-Catalyzed Dehydration of Alcohols", J. Org, Chem., 32, pp. 3386-3389 (1967) discloses that the thoria-catalyzed dehydration of secondary 2-alcohols is selective for α-olefins, and that the amount of ketone by-product is low, and Davis, "Catalytic Conversion of Alcohols. 11. Influence of Preparation and Pretreatment on the Selectivity of Zirconia", Ind. Eng. Chem. Prod. Res. Dev., Vol. 18, No. 3, pp. 181-198 (1979) discloses that a zirconia catalyst is similar to thoria for both the dehydration and α-olefin selectivity in the conversion of 2-alcohols to olefins.

Other methods of preparing α-olefins are also known. For example, British Patent Specification No. 1,233,020, published May 26, 1971, discloses a method for making 4-methylpentene-1 by subjecting a mixture of acetone and isobutyraldehyde to conditions under which acetone undergoes condensation both with itself to form diacetone alcohol and with isobutyraldehyde to form the acetone/isobutyraldehyde condensate methyl, 2-methyl 3-hydroxy butyl ketone, subjecting the mixed condensates to conditions under which they undergo dehydration to the corresponding olefinically unsaturated ketones, hydrogenating these ketones to saturated alcohols and dehydrating these saturated alcohols over alkalized alumina to form a mixture of 4-methyl-pentenes-1 and -2 and a mixture of methylhexenes.

A process for producing $C_5$ to $C_{18}$ straight chain α-olefins has now been discovered which provides these olefins in useful quantities.

SUMMARY OF THE INVENTION

In accordance with the present invention, there is provided a process for making $C_5$ to $C_{18}$ straight chain α-olefins comprising: selectively cracking a mixture comprising (1) $C_5$ to $C_{18}$ straight chain, saturated compounds having an electrophilic group in the 2 position and (2) $C_5$ to $C_{18}$ straight chain, saturated compounds having an electrophilic group in a 3+ position under conditions whereby substantially more of the compounds having the electrophilic group at the 2 position are converted to olefins than are the compounds having the electrophilic group at a 3+ position.

In accordance with the present invention, there is further provided a process for making $C_5$ to $C_{18}$ straight chain α-olefins comprising:

A. reacting an olefinic reactant comprising a $C_5$ to $C_{18}$ straight chain β-olefin or mixture of $C_5$ to $C_{18}$ straight chain α-olefin and $C_5$ to $C_{18}$ straight chain β-olefin with an electrophilic compound containing reactive hydrogen under conditions which permit the electrophilic compound containing reactive hydrogen to add to carbon-carbon double bonds to produce a mixture comprising saturated $C_5$ to $C_{18}$ straight chain compounds having an electrophilic group at the 2 position and saturated $C_5$ to $C_{18}$ straight chain compounds having an electrophilic group at a 3+ position; and B. selectively cracking the product of step A under conditions whereby substantially more of the compounds having the electrophilic group at the 2 position are converted to olefins than are the compounds having the electrophilic group at a 3+ position.

In accordance with the present invention, there is also provided a process for making $C_5$ to $C_{18}$ straight chain $\alpha$-olefins comprising:

A. reacting an olefinic reactant comprising a $C_5$ to $C_{18}$ straight chain $\beta$-olefin or mixture of $C_5$ to $C_{18}$ straight chain $\alpha$-olefin and $C_5$ to $C_{18}$ straight chain $\beta$-olefin with an electrophilic compound containing reactive hydrogen under conditions which permit the electrophilic compound to add to carbon-carbon double bonds, said electrophilic compound being hydrolyzable to an alcohol after addition to the carbon-carbon double bond, to produce a mixture comprising saturated $C_5$ to $C_{18}$ straight chain compounds having a hydrolyzable electrophilic group at the 2 position and saturated $C_5$ to $C_{18}$ straight chain compounds having a hydrolyzable electrophilic group at a 3+ position;

B. hydrolyzing the product of step A to reduce the product of step A to a mixture of alcohols; and C. selectively cracking the product of step B under conditions whereby substantially more of the compounds having the hydroxyl group at the 2 position are converted to olefins than are the compounds having the hydroxyl group at a 3+ position.

The present invention further provides a process for making $C_5$ to $C_{18}$ straight chain $\alpha$-olefins comprising:

A. reacting an olefinic reactant comprising a $C_5$ to $C_{18}$ straight chain $\beta$-olefin or mixture of $C_5$ to $C_{18}$ straight chain $\alpha$-olefin and $C_5$ to $C_{18}$ straight chain $\beta$-olefin with an electrophilic reactant selected from the group consisting of water and a hydrolyzable electrophilic compound containing reactive hydrogen under conditions which permit the electrophilic reactant to add to carbon-carbon double bonds to produce a mixture comprising saturated $C_5$ to $C_{18}$ straight chain alcohols having an electrophilic group at the 2 position and saturated $C_5$ to $C_{18}$ straight chain alcohols having an electrophilic group at a 3+ position;

B. when the electrophilic reactant employed in step A is a hydrolyzable electrophilic compound containing reactive hydrogen, hydrolyzing the product of step A to form alcohols;

C. converting the alcohols to alkyl xanthates; and

D. selectively cracking the product of step C under conditions whereby substantially more of the compounds having the xanthate group at the 2 position are converted to olefins than are the compounds having the xanthate group at a 3+ position.

DETAILED DESCRIPTION OF PREFERRED EMBODIMENTS

The starting material employed in the processes of the present invention comprises $C_5$ to $C_{18}$ straight chain $\beta$-olefin or a mixture of $C_5$ to $C_{18}$ straight chain $\alpha$-olefin and $C_5$ to $C_{18}$ straight chain $\beta$-olefin (hereafter referred to simply as the "$C_5$ to $C_{18}$ straight chain olefin reactant"). Typically, the starting material will be a mixture of $C_5$ to $C_{18}$ straight chain olefin isomers (i.e., the position of the double bond may not be the same in each molecule), since such mixtures are readily available from commercial processes. The source of the starting mixture is not critical. It could come from various cracking operations such as fluid catalytic cracking or steam cracking. A particularly suitable source is from the dehydrogenation or chlorination/dehydrochlorination of n-paraffins. Mixtures of olefin dimers, such as those produced by the nickel catalyzed dimerization of olefins, are also suitable as starting materials.

The starting materials (feed) may consist of olefins having the same carbon number or a mixture of olefins of different carbon number in the $C_5$ to $C_{18}$ range However, the $C_5$ to $C_{18}$ straight chain olefin reactant must contain some amount of a $\beta$-olefin. As used herein the term "$\beta$-olefin" refers to $C_5$ to $C_{18}$ straight chain olefins which have a carbon-carbon double bond between the second and third carbon atoms in the chain. It is these $\beta$-olefins which ultimately yield the desired $\alpha$-olefin. The $\beta$-olefin is preferably present in olefin mixtures which are available from the commercial sources noted above. It is, however, possible to start with a mixture of olefins which contains neither $\alpha$-olefins nor $\beta$-olefins. In that case, the olefin mixture is reacted with an electrophilic compound containing reactive hydrogen under conditions which permit said electrophilic compound to add to carbon-carbon double bonds. The resulting product is then cracked to produce another mixture of olefins. However, in this mixture of olefins, at least some of the double bonds will be closer to the end of the carbon chain than in the original mixture of olefins. This electrophilic compound/cracking procedure can thus be repeated until the resulting mixture of olefins contains some $\beta$-olefins. This mixture may then be used as the $C_5$ to $C_{18}$ straight chain olefin reactant in the practice of the present invention.

The $C_5$ to $C_{18}$ straight chain olefin reactant is reacted with an electrophilic compound containing reactive hydrogen. Examples of suitable electrophilic compounds containing reactive hydrogens include, but are not limited to, water, carboxylic acids (such as formic acid, acetic acid, trimethylacetic acid, and dimethylbutyric acids), and sulfuric acid. The electrophilic compound containing reactive hydrogen is reacted with the $C_5$ to $C_{18}$ straight chain olefin reactant under conditions which permit it to add to the carbon-carbon double bond in the $C_5$ to $C_{18}$ straight chain olefin. This produces a mixture of saturated $C_5$ to $C_{18}$ straight chain compounds having an electrophilic group at the 2 position (a "2-isomer"), i.e., the electrophilic group is on a carbon atom which is adjacent to the end carbon atom of the chain, and saturated $C_5$ to $C_{18}$ straight chain compounds having an electrophilic group in a 3+ position (a "3+ isomer"). As used herein, the term "3+ position" means that the electrophilic group is on a carbon atom which is at least the third (or farther) carbon atom from the end of the chain. By way of example, when the $C_5$ to $C_{18}$ straight chain olefin reactant is a mixture of n-hexenes, e.g., a mixture of 1-, 2- and 3-hexene, the resulting reaction product comprises a mixture of 2- and 3-hexyl isomers

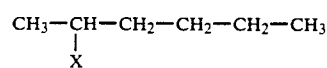

and

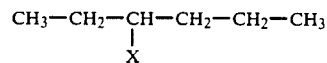

where X is the negative group (e.g., —OH, —OOCCH$_3$ or HSO—$_4$) from the electrophilic compound containing reactive hydrogen.

The conditions for the addition of the electrophilic compound to the olefins are well known in the art. Generally, acid catalysis is useful. This can often be provided by the electrophilic compound itself.

The electrophilic compounds containing reactive hydrogen useful in this invention fall into two general categories. The first category comprises compounds which, after they have added to the double bonds in the C$_5$ to C$_{18}$ straight chain olefin reactant, can be removed directly by cracking the 2- and 3-isomers. Compounds which fall into this category include, but are not limited to, water and carboxylic acids, such as formic acid, acetic acid, trimethylacetic acid, and dimethylbutyric acids. (In some cases, it may be desirable, though not necessary, to hydrolyze the electrophilic compounds in this first category, such as the carboxylic acids, to alcohols prior to cracking.) The second category of electrophilic compounds containing reactive hydrogen comprises compounds which add to the double bonds in the C$_5$ to C$_{18}$ straight chain olefin reactant, but which are not readily removed from the resulting product by cracking, e.g., sulfuric acid. When this second category of compounds is used, the product is subjected to an intermediate step, such as hydrolysis, to convert the negative group from the electrophilic compound containing reactive hydrogen (i.e., X in the above formulas) to a group, such as hydroxyl, which can be readily removed by cracking.

Once the product made by the reaction of the C$_5$ to C$_{18}$ straight chain olefin reactant with the electrophilic compound containing reactive hydrogen contains a group which is readily removed by cracking, that product can be cracked. The cracking step is critical in the process of the present invention since it "selectively" cracks the 2-isomer (to produce olefins). Under ideal "selective cracking" conditions, only the 2-isomer is converted to olefin, with the 3+ isomer remaining intact. However, under normal conditions, it is not possible to prevent cracking of the 3+ isomer altogether. Thus, conditions are chosen such that substantially more of the 2-isomer is cracked to olefin than is the 3+ isomer. Typically, conditions which permit conversion of about 60 to about 90% of the 2-isomer to olefin are chosen. Such conditions provide a relatively high conversion of 2-isomer to olefin while keeping the conversion of 3+ isomer to olefin acceptably low.

It has been found that when a mixture of 2-isomer and 3+ isomers is cracked, the 2-isomer reacts faster than the 3+ isomers. Thus, the simplest way to "selectively" crack the 2-isomer (but not a major amount of the 3+ isomers) is to conduct the cracking for a period of time sufficiently long for most of the 2-isomer to react, but only long enough for a minor amount, i.e., less than 50%, of the 3+ isomers to react.

In the practice of the present invention, the 2-isomer is "partially" converted to olefin. "Partial" conversion means that less than about 99% of the 2-isomer is converted to olefin. Preferably, about 90% to about 99% of the 2-isomer is converted to olefin, though conversions as low as about 60% to about 90% are acceptable. This partial conversion of the 2-isomer to olefin is accomplished by an appropriate choice of temperature and space velocity in a continuous process, and temperature and time in a batch process. The cracking reaction rates for the 2-isomer and 3+ isomer are different, and this difference can be magnified by operating at a relatively low temperature with an appropriately longer contact time.

One of the advantages of the process of the present invention is that the conversion of the 3+ isomer to olefin is significantly reduced relative to that of the 2-isomer. The highest ratio of 2-isomer conversion to 3+ isomer conversion is achieved at very low overall conversion levels of both isomers. However, conducting the process at these low overall conversion levels would be undesirable from an economic standpoint. Thus, based on practical considerations, the conversion rate of 2-isomer to olefin should be set between about 60 and 99%.

Depending upon the particular readily removable group which is present, removal of the group may be accomplished by simple thermal cracking or by a cracking procedure which utilizes a catalyst. For example, when acetic acid is used as the electrophilic compound containing reactive hydrogen, thermal cracking may be used. When water is used as the electrophilic compound containing reactive hydrogen, the resulting products are alcohols. The cracking of these alcohols if preferably conducted in the presence of a mildly basic metal oxide catalyst.

The materials useful as cracking catalysts should not be acidic or strongly basic. Acid catalysts can isomerize the $\alpha$-olefin product to internal olefins, which is undesirable. If a strongly basic catalyst is used, appreciable dehydrogenation of the alcohol could occur, which is undesirable. Thus, suitable catalysts are mildly basic metal oxides which do not cause appreciable dehydrogenation of the alcohol and which exhibit selectivity for the production of $\alpha$-olefins. This general type of catalyst is discussed in an article by Burtron H. Davis entitled "Alcohol Conversion Selectivity as a Measure of the Base Strength of Metal Oxide Catalysts" in Che et al., *Adsorption and Catalysis on Oxide Surfaces* (1985); which article is incorporated by reference herein in its entirety. Examples of mildly basic metal oxides suitable as catalysts in this invention include the oxides of Y, Zr, La, In, Ce, Pr, Nd, Sm, Eu, Dy, Ho, Yb and Th. Suitable cracking temperatures range from about 200° to about 450° C., preferably from about 250° to about 400° C.

It has been found that hydrous zirconium oxide prepared by a particular technique is an especially suitable catalyst. This catalyst is prepared by precipitating/digesting soluble ZrO(NO$_3$)$_2$ at high pH above room temperature (e.g., about 50°–75° C.), washing the resulting product thoroughly with both aqueous ammonia and water and drying exhaustively (e.g., at 80° C. or higher under vacuum for at least 16 hours). Before use, the catalyst is calcined at about 350°–650° C. This catalyst provides excellent conversion of 2-alcohols to olefin as well as excellent selectivity for $\alpha$-olefin in the product.

When the C$_5$ to C$_{18}$ straight chain olefin reactant is a mixture of C$_6$ olefin isomers, the above-described process can be depicted by the following general reaction scheme. This general reaction scheme is illustrative only and is not intended to limit the present invention in any way.

STEP 1

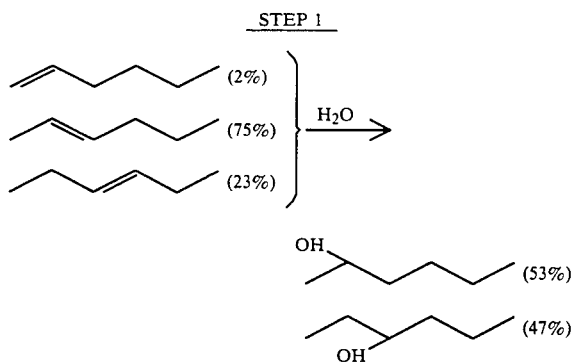

In the above Step 1, the percentages in parentheses refer to the relative amounts of 1-, 2- and 3-hexene, i.e., the weight percentages of 1-, 2- and 3-hexene based on the total weight of 1-, 2- and 3-hexene.

The yield of 2-hydroxyhexane (which ultimately can yield 1-hexene) in Step 1 (53 wt. % of the total product) is not substantially higher than the yield which would be expected for random addition of the water to the double bonds, i.e., about 50% of the alcohols produced would be expected to be 2-hydroxyhexane if random addition occurred. However, it has been found that the amount of 2-isomer in this product can be increased significantly above this random level by using an electrophilic compound containing reactive hydrogen other than water. For instance, if acetic acid is used, the product contains about 63% of the 2-isomer and 37% of the 3-isomer. Using sulfuric acid as the electrophilic compound containing reactive hydrogen yields a product containing about 73% of the 2-isomer and 27% of the 3-isomer. The use of "bulky" acids, such as trimethylacetic acid or dimethylbutyric acids, should likewise increase the amount of 2-isomer in the product.

The product of Step 1 is next selectively cracked to produce a mixture comprising 1-hexene and 3-hydroxyhexane, as well as some amount of 2-hexene and 3-hexene. The relative amounts of these compounds will depend upon the cracking conditions employed.

STEP 2

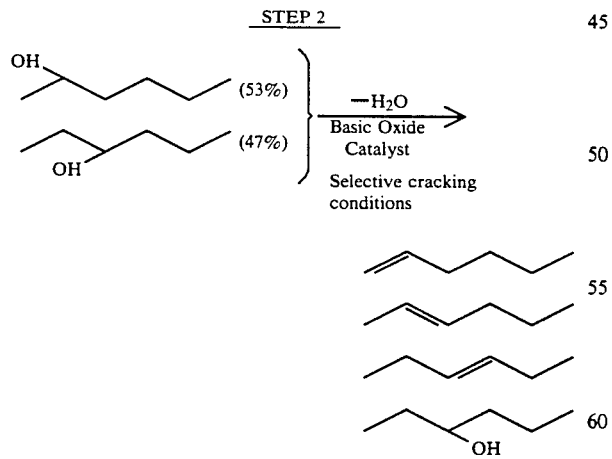

Should it be desirable to separate the 1-hexene from the product of step 2, this can be accomplished by techniques such as distillation or adsorption which are well known in the art.

The process of the present invention may be conducted either as a batch process or in a continuous manner. It is generally preferable to conduct the process in a continuous manner. The product of the cracking step will generally contain some quantity of β-olefin and/or olefins having their double bond farther from the end of the chain than the β position. Also, some compounds which were not cracked and still contain the electrophilic group of the electrophilic compound containing reactive hydrogen (e.g., alcohols) may be present. Thus, the process of this invention is advantageously conducted by recovering the desired product, α-olefin, from the product of the cracking step, and recycling any remaining olefins and uncracked compounds to be used as a portion of the feed for the reaction with the electrophilic compound containing active hydrogen. This may be accomplished by recycling these compounds to a point in the process where they will become part of the original starting material, or to a point before reaction with the electrophilic compound containing reactive hydrogen. In this way the amount of α-olefin produced from a given mixture of olefins is maximized.

The present invention is further illustrated by the following example in which all percentages are by weight unless otherwise stated.

EXAMPLE 1

In this experiment, an alcohol feed was used which consisted of 50% 2-hexanol and 50% 3-hexanol. This feed was cracked using a lanthanum oxide powder cracking catalyst supported on quartz chips. The conditions were controlled so that about 70% of the 2-hexanol was cracked to hexene. Under these conditions, only about 25% of the 3-hexanol in the feed mixture was cracked to hexenes.

What is claimed is:

1. A process for making $C_5$ to $C_{18}$ straight chain α-olefins comprising: selectively cracking a mixture comprising (1) $C_5$ to $C_{18}$ straight chain, saturated compounds having an electrophilic group in the 2 position and (2) $C_5$ to $C_{18}$ straight chain, saturated compounds having an electrophilic group in a 3+ position under conditions whereby substantially more of the compounds having the electrophilic group at the 2 position are converted to olefins than are the compounds having the electrophilic group at a 3+ position.

2. A process for making $C_5$ to $C_{18}$ straight chain α-olefins comprising:
   A. reacting an olefinic reactant comprising a $C_5$ to $C_{18}$ straight chain β-olefin or mixture of $C_5$ to $C_{18}$ straight chain α-olefin and $C_5$ to $C_{18}$ straight chain β-olefin with an electrophilic compound containing reactive hydrogen under conditions which permit the electrophilic compound containing reactive hydrogen to add to carbon-carbon double bonds to produce a mixture comprising saturated $C_5$ to $C_{18}$ straight chain compounds having an electrophilic group at the 2 position and saturated $C_5$ to $C_{18}$ straight chain compounds having an electrophilic group at a 3+ position; and
   B. selectively cracking the product of step A under conditions whereby substantially more of the compounds having the electrophilic group at the 2 position are converted to olefins than are the compounds having the electrophilic group at a 3+ position.

3. The process of claim 2 further comprising separating α-olefin from the product of the cracking step and recycling the remainder of said product to form a portion of the material used to react with the electrophilic compound containing reactive hydrogen.

4. A process for making $C_5$ to $C_{18}$ straight chain α-olefins comprising:
  A. reacting an olefinic reactant comprising a $C_5$ to $C_{18}$ straight chain β-olefin or mixture of $C_5$ to $C_{18}$ straight chain α-olefin and $C_5$ to $C_{18}$ straight chain β-olefin with an electrophilic compound containing reactive hydrogen under conditions which permit the electrophilic compound to add to carbon-carbon double bonds, said electrophilic compound being hydrolyzable to an alcohol after addition to the carbon-carbon double bond, to produce a mixture comprising saturated $C_5$ to $C_{18}$ straight chain compounds having a hydrolyzable electrophilic group at the 2 position and saturated $C_5$ to $C_{18}$ straight chain compounds having a hydrolyzable electrophilic group at a 3+ position;
  B. hydrolyzing the product of step A to reduce the product of step A to a mixture of alcohols; and
  C. selectively cracking the product of step B under conditions whereby substantially more of the compounds having the hydroxyl group at the 2 position are converted to olefins than are the compounds having the hydroxyl group at a 3 + position.

5. The process of claim 4 wherein the electrophilic compound is sulfuric acid or a carboxylic acid.

6. The process of claim 4 further comprising separating α-olefin from the product of the cracking step and recycling the remainder of said product to form a portion of the material used to react with the electrophilic compound.

7. A process for making $C_5$ to $C_{18}$ straight chain α-olefins comprising:
  A. reacting an olefinic reactant comprising a $C_5$ to $C_{18}$ straight chain β-olefin or mixture of $C_5$ to $C_{18}$ straight chain α-olefin and $C_5$ to $C_{18}$ straight chain β-olefin with an electrophilic reactant selected from the group consisting of water and a hydrolyzable electrophilic compound containing reactive hydrogen under conditions which permit the electrophilic reactant to add to carbon-carbon double bonds to produce a mixture comprising saturated $C_5$ to $C_{18}$ straight chain alcohols having an electrophilic group at the 2 position and saturated $C_5$ to $C_{18}$ straight chain alcohols having an electrophilic group at a 3+ position;
  B. when the electrophilic reactant employed in step A is a hydrolyzable electrophilic compound containing reactive hydrogen, hydrolyzing the product of step A to form alcohols;
  C. converting the alcohols to alkyl xanthates; and
  D. selectively cracking the product of step C under conditions whereby substantially more of the compounds having the xanthate group at the 2 position are converted to olefins than are the compounds having the xanthate group at a 3 + position.

8. The process of claim 7 wherein the reactant in step A is selected from water, sulfuric acid, and carboxylic acids.

9. The process of claim 7 further comprising separating α-olefin from the product of the cracking step and recycling the remainder of said product to form a portion of the material used to react with the electrophilic reactant.

10. The process of claim 1 wherein the electrophilic group is selected from hydroxyl, sulfate, carboxylate and xanthate groups.

11. The process of claim 2 wherein the electrophilic compound is selected from the group consisting of water and carboxylic acids.

12. The process of claim 1, 2, 3, 4 or 6 wherein the cracking is conducted in the presence of a mildly basic metal oxide catalyst capable of selectively producing α-olefins.

13. The process of claim 2, 3, 4, 6, 7, 9, 10 or 11 wherein the olefinic reactant is a mixture of n-hexenes.

* * * * *